United States Patent [19]

Spallholz

[11] 4,341,757
[45] Jul. 27, 1982

[54] STABLE ISOTOPIC IMMUNOASSAY METHOD EMPLOYING NON-RADIOACTIVE SELENIUM LABEL

[75] Inventor: Julian E. Spallholz, Lubbock, Tex.

[73] Assignee: Nutrition 21, San Diego, Calif.

[21] Appl. No.: 183,467

[22] Filed: Sep. 2, 1980

[51] Int. Cl.$^3$ .................... G01N 33/52; G01N 33/54
[52] U.S. Cl. .......................................... 424/8; 424/1; 424/12; 424/13; 23/230 B; 250/302; 250/304; 250/461.2; 356/39; 356/432
[58] Field of Search ............... 424/1, 8, 12; 23/230 B; 250/302, 304; 356/39, 432

[56] References Cited

U.S. PATENT DOCUMENTS 4,166,820  9/1979  Spallholz .......................... 260/326.4

Primary Examiner—Anna P. Fagelson
Attorney, Agent, or Firm—Fischer, Tachner & Strauss

[57] ABSTRACT

There is disclosed a "cold", i.e., non-radioactive (stable) isotope method for the immunoassay of biological compounds. The method uses selenium as the tracer label in compounds which compete in reaction with a conjugating compound and thus yield a solution for analysis which is a mixture of complexes of the conjugating compound with the selenium labelled and unlabelled compound. The nonradioactive isotope can be analyzed using fluorimetric determinations with proper preparatory treatment or atomic adsorption. Selenium is particularly unique in its adaptability to this assay because of its great compatibility with biochemicals, e.g., it has an atomic size and structure and chemical properties very close to that of sulfur and it readily forms compounds and small adducts with carbon and hydrogen containing compounds. Selenium is also ideally suited for use in this assay because it can be quantitatively detected at extremely low concentrations, e.g., the lower detection limit is presently about $10^{-9}$ to $10^{-10}$ grams per milliliter.

12 Claims, No Drawings

STABLE ISOTOPIC IMMUNOASSAY METHOD EMPLOYING NON-RADIOACTIVE SELENIUM LABEL

BACKGROUND OF THE INVENTION

This invention relates to a method of immunoassay and, in particular, to a method of competitive immunoassay using a "cold", i.e., non-radioactive selenium labelled compounds.

Radioimmunoassay was first used as a clinical procedure about 1960 and today is in widespread use. This analytical method provides high accuracy and specificity for detecting complex biochemicals, characteristics which have led to its rapid acceptance. The method, however, has some negative features. Among these are: the short shelf life of some radioactive tracers, typically radioactive isotopes of iodine, radiolysis of the labelled compounds, and the disposal problems of the used radioisotopes. One of the most widely used radioactive tracers is $^{125}I$ (iodine) and a significant number of biochemicals such as some antigens and haptens can not be conveniently labelled with this tracer.

The radioimmunoassay procedure comprises admixing a known amount of a radioactive labelled reactive compound with the biological sample containing a compound of unknown concentration. The resultant mixture is incubated and the labelled and unlabelled rreactive compounds compete in complexing with a conjugating compound. After the incubation period, the solution is treated to remove excess or unreacted amoounts of the labelled and unlabelled reactive compounds and then is analyzed for the proportions of labelled and unlabelled reactive compounds in the complexes; these proportions reflecting the original concentrations of the labelled compound, which is known, and of the unlabelled compound, which can thus be determined from known standard concentrations of the compound.

BRIEF DESCRIPTION OF THE INVENTION

This invention comprises an immunoassay using a "cold" or non-radioactive selenium isotope ($^{79}Se$) as the tracer in a labelled compound to compete in complex formation with unlabelled compound in the formation of complexes with a conjugating compound. Selenium can be incorporated into an extremely wide variety of biochemical compounds such as haptens, antigens and antibodies which can be used in a competitive immunoassay. In this assay, a known amount of a selenium labelled compound and a limited amount of a conjugating compound are added to the biological sample, e.g., serum, of the compound under investigation. The resultant mixture is incubated to react the compounds and form preparations of the labelled and unlabelled compounds. The incubated solution is then treated to remove unreacted quantities of the complexed or labelled compounds, e.g., by contacting with a solid adsorbent, and the solution is then analyzed to determine its content of the complex of the labelled compound and of selenium. The amount of unlabelled reactive compound in the original biological sample can then be determined by proportionation to the contents of labelled and unlabelled complexes. Preferred selenium compounds which can be used to synthesize the tracer labelled reactive compounds are N-succinimidyl-alkylselenoesters such as are disclosed and claimed in my earlier patent, U.S. Pat. No. 4,166,820.

DESCRIPTION OF PREFERRED EMBODIMENTS

Selenium readily forms adducts and compounds with organic compounds because of its atomic size and structure which is closely related to sulfur. Selenium is also very compatible with carbon and hydrogen bonds. In my earlier patent, I disclosed classes of selenium compounds which have a high reactivity for proteins, polypeptides and the like to permit bonding of selenium to haptens, antibodies and antigens, thereby permitting the use of selenium as a tracer in competitive immunoassays. The readily apparent application of these compounds is with radioactive isotopes of selenium in radioimmunoassay procedures and selenium compounds such as disclosed in my earlier patent have a number of advantages over the prior radioactive tracers of iodine, carbon, etc.

The present invention utilizes cold, i.e., non-radioactive isotopes of selenium ($^{79}Se$) as the tracer element in labelled reactive biochemicals such as antigens, haptens, antibodies, etc. The selenium is a weighted isotope mixture of the following selenium isotopes:

TABLE 1

| Isotope | Weight Percent |
|---------|----------------|
| 80 | 48 |
| 78 | 50 |
| 76 | 10 |
| 82 | 9 |
| 77 | 8 |
| 76 | 1 |

Useful selenium compounds are those disclosed in my earlier application having the general formula:

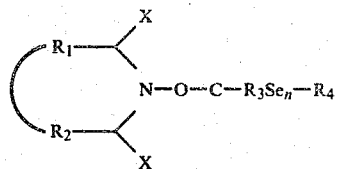

wherein:

X is hydrogen or oxo;

$R_1$ and $R_2$, together, are ethylene, trimethylene, or 5,6-phenylene;

$R_3$ is alkylene of 1 to 6 carbons $R_4$ is alkyl or isoalkyl of 1 to 6 carbons, phenyl or benzyl; or $R_3$ and $R_4$ together are 1,2,3-propanetriyl; and n is 1 or 2.

Examples of suitable compounds of the aforementioned class are: N-succinimidyl-ethylselenoacetate, N-succinimidyl-3-(methylseleno)-propionate, N-succinimidyl-3-(isopropylseleno) propionate, N-phthalidyl-3-(ethylseleno) propionate, N-phthalmidyl-methylseleno acetate, N-piperidyl-3-(ethylseleno) butyrate, etc. These selenium compounds readily combine with proteins, haptens, antibodies and antigens by admixing the selenium compound with the biochemical compound, e.g., a protein, in the presence of sodium borate as a buffer. The seleno compound is added in molar excess and glycine is added after reaction to react with the excess compound. The selenocompound-protein adduct can be purified by gel filtration or dialysis to obtain the useful, seleno labelled reactive compound for use in the immunoassay method.

Selenium may also be incorporated into reactive biochemicals such as cyclic nucleotides by reaction of a cyclic nucleotide with NaHSe followed by treatment with methyl iodide, dithiothreitol and sodium carbonate. The resultant selenium labelled cyclic nucleotide can be purified by chromotography techniques. Cortisol can be labelled with selenium by reaction of cortisol acetate with selenium dioxide or selenic acid, followed by methyl iodide and dithiothreitol treatment. The competitive immunoassay procedure uses essentially the same sample preparation as used in radioimmunoassays. A representative sample of the biological fluid, such as a serum sample for assay of a specific biochemical is admixed with a limited quantity of the conjugating compound and a known quantity of the selenium labelled biochemical. In a typical analysis, a sample from 100 to about 200 microliters is admixed with about 100 microliters of a conjugating compound and from 20 to about 600 nanograms of the selenium labelled compound. The resultant mixture is incubated for a sufficient time to permit reaction, generally from 5 to about 60 minutes, preferably from about 10 to about 20 minutes, at a temperature from about 25 to about 32 degrees C. After incubation, the solution is treated to remove excess, unreacted quantities of the selenium labelled biochemical. A suitable treatment is to contact the solution with an adsorptive solid such as charcoal. Following the removal of the unreacted biochemical the solution is analyzed for its contents of the complex between the conjugating compound and biochemical and for its content of selenium.

The quantity of the complex present in the serum is determined by analyzing the solution after charcoal treatment or centrifugation and comparing to a set of sample standards of known concentration.

The selenium content of the solution can also be determined by atomic adsorption or by fluorometric techniques. In the latter method, the sample is digested in a boiling solution of nitric and perchloric acids. The selenium in the complex is oxidized and reduced to selenite which is reacted with diaminonaphthalene to obtain 4,5-benzopiazselenol which is measured by fluorescent analysis.

The biochemicals which can be analyzed by the cold isotope immunoassay thus described are extensive. Essentially any of the biochemicals which can be assayed by radioimmunoassay can similarly be assayed by the method of this invention. This includes any biochemical compound which specifically reacts with a specific conjugating compoound. The following table lilsts some of the compounds which may be assayed by this method:

TABLE 2

Peptide Hormones

Growth hormone
Adrenocorticotropic hormone
Melanocyte stimulating hormone

Glycoproteins

Prolactin
Lipotropin

Calcitropic Hormones

Parathyroid hormone
Calcitonin

Pancreatic Hormones

Insulin
Proinsulin
C-Peptide
Glucagon

Chorionic Hormones

Human chorionic gonadotropin
Human chorionic somatomammotropin

Gastrointestinal Hormones

Gastrin
Secretin
Cholecystokinin-pancreozymin
Enteroglucagon
Gastric inhibitory polypeptide

Vasoactive Tissue Hormones

Angiotensins
Bradykinins

Hypothalamic Releasing Factors

Thyrotropin releasing factor
Growth-hormone-release inhibiting factor
Gonadotropin releasing factor

NonPeptidal Hormones

Thyroidal Hormones

Triiodothyronine (Tz)
Thyroxine (Ty)

Prostaglandins

Steroids

Aldosterone
Corticosteroids
Estrogens
Androgens
Progesterones

NonHormonal Biochemicals

Drugs

Cardiac glycosides
Morphine
LSD
Barbiturates
Chlorpromazine
Nicotine
Penicillin & Gentamicin
D-tybocurarine

Cyclic Nucleotides

Adenosine 5'-monophosphate
Guanosine 5'-monophosphate
Inosine 5'-monophosphate
Unidine 5'-monophosphate

Enzymes

C esterase
Fructose 1,6-diphosphatase
Pleshminogen and Plasmin
Chymotrypsin
Trypsin
Carbonic anhydrase isoenzymes

Viruses

Hepatitis B antigen

Tumor Antigens

Carcinoembryonic antigen
alpha-Fetoprotein

Serum Proteins

Thyroxin binding globulin
Properdin
Fibrinogen
Anti-Rh antibodies

Other Biochemicals

Intrinsic factor
Rheumatoid factor
Hagerman factor
Neurophysine
Folic acid
Calcium binding protein
Stephylococcal
beta-Enterotoxin Conjugating compounds for each of the foregoing biochemical compounds are known and available, or can be readily made. The conjugating compound is generally identified by use of the prefix "anti-" thereby identifying a specific anti-body, e.g., anti-folic acid, anti-insulin, etc.

The invention will now be illustrated by specific examples which will demonstrate the specific mode of application.

EXAMPLE 1

A biochemical-binding selenium compound is prepared by admixing 3.34 parts of 3-methylselenopropionic acid with 2.3 parts of N-hydroxysuccinimide in 25 parts of dry tetrahydrofuran. The mixture is stirred continuously in an acetone-dry ice bath. Then, 4.95 parts of dicyclohexylcarbodimide is added and the mixture is stirred overnight at a temperature of about 0 degrees C. Thereafter, 0.5 parts acidic acid and 40 parts of ethyl acetate are added and the mixture is stirred for one hour, and filtered to remove N,N'-dicyclohexylurea. The filtered solid is washed with ethyl acetate, the washings are combined with the filtrate and the filtrate is evaporated to obtain a residue which is dissolved in 100 parts dry methanol. The methanol solution is boiled, charcoal is added and the mixture is filtered. The filtrate is cooled in an ice bath and N-succinimidyl-3-(methylseleno)propionate is precipitated and purified.

EXAMPLE 2

A selenium labelled protein such as insulin is quantitated and prepared by admixing 5 parts of insulin with 100 parts of the N-succinimidyl-3-(methylseleno)-propionate in 10 parts of 0.1 Molar sodium borate (buffer at pH=8.5) solution at 0 degrees C. Thereafter, 0.5 parts of 0.2 Molar glycine buffered at pH of 8.5 is added to react with any unreacted quantities of the selenium compound and the reaction product, selenoinsulin, is purified by dialysis or chromotography.

EXAMPLE 3

A competitive immunoassay is performed using the selenium labelled insulin prepared in the preceding example. In this procedure, labelled insulin is quantitated and diluted to appropriate concentration with buffered phosphate (pH=7.4) containing 0.5 percent bovine serum albumin. The mixture is added to a set of insulin standards up to 50 nanograms of insulin in 500 microliters of serum which have been appropriately diluted and mixed. First and second insulin complexing agents are added to the mixtures and the resultant mixtures are incubated at ambient temperature. Following centrifugation, the precipitated insulin complexes can be quantitated by fluorimetric or atomic adsorption techniques. Serum insulin is quantitated by comarison of the amount of selenium in the serum sample as compared to the insulin standards.

EXAMPLE 4

Selenium hydrocortisone acetate is prepared by refluxing 2 parts hydrocortisone acetate and 1 part selenium dioxide in 20 parts glacial acetic acid for 1 hour followed by crystallization of the selenium hydrocortisone acetate from ethanol. The same compound can also be obtained commercially.

EXAMPLE 5

Standard serum solutions of Selenium ($^{75}$Se) hydrocortisone acetate (cortisol) containing 23, 7.3, 19.6, and 57 micrograms cortisol per 100 milliliters and 3.5, 11.4, 30.0 and 89.0 nanograms selenium per milliliter were diluted and incubated using the competitive protein binding method. Endogenous transcortin was denatured by heating at 70 degrees C. for 10 minutes. Following incubation with the competitive binding protein, addition of adsorbent granular material and centrifugation, the cortisol standards and unknown serum samples were quantitated for $^{75}$selenium by both gamma scintillation and fluorescence measurements. Detection of selenium by gamma scintillation and fluorescence measurements of $^{75}$selenium cortisol were compared. The fluorescence method, while not as sensitive as the scintillation method, was sufficiently sensitive for quantitation of cortisol in this competitive protein binding assay. The present detection limits for $^{79}$selenium by fluorescence is 1 nanogram and by graphite atomic absorption is 50 picograms.

The invention has been described with reference to the illustrated and preferred mode of practice. It is not intended that the invention be unduly limited by this disclosure of the presently preferred mode of practice. Instead, it is intended that the invention be defined by the elements, and their obvious equivalents set forth in the following claims.

What is claimed is:

1. In a competitive immunoassay wherein at least one standard solution and at least one unknown solution of a reactive biological compound are admixed with known quantities of tracer labelled reactive biological compound and a conjugating compound which forms a complex with said reactive biological compound, the resultant mixtures are incubated and said solutions are treated to remove unreacted quantities of reactive biological compound and are analyzed for their contents of labelled and unlabelled complexes, the improvement which comprises the use of a non-radioactive selenium labelled binding compound as said tracer labelled reactive biological compound and analyzing for selenium in the complexes which are obtained by atomic adsorption or fluorometric analyses.

2. The immunoassay of claim 1 wherein said selenium labelled compound is a compound of a mixture of selenium isotopes having a weighted average atomic number of 79.

3. The method of claim 1 wherein said selenium is analyzed by fluorometric measurement.

4. The method of claim 3 wherein said measurement is performed on samples prepared by converting the selenium in the complexes to selenites, reacting the selenites with diaminonaphthalene to obtain 4,5-benzopiazselenol for said fluorometric measurement.

5. The method of claim 1 wherein said solutions after incubation are contacted with charcoal to remove unreacted quantities of reactive biological compound.

6. The immunoassay of claim 1 wherein said selenium binding compound is selected from the class consisting of selenium labelled antigens, haptens and antibodies.

7. The immunoassay of claim 2 wherein said selenium binding compoound is a conjugate of an antigen, hapten or antibody with a selenium compound of the formula:

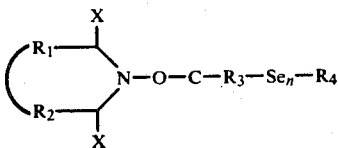

wherein:
X is hydrogen or oxo;
$R_1$ and $R_2$, together, are ethylene, trimethylene, or 5,6-phenylene;
$R_3$ is alkylene of 1 to 6 carbons;
$R_4$ is alkyl or isoalkyl of 1 to 6 carbons, phenyl or benzyl; or
$R_3$ and $R_4$ taken together are 1,2,3-propanetriyl; and n is 1 or 2.

8. The method of claim 7 wherein X is oxo.

9. The method of claim 8 wherein said selenium compound is a N-succinimdyl alkylselenoester.

10. The method of claim 8 wherein said selenium compound is a N-phthalimidyl alkylselenoester.

11. The method of claim 7 wherein said selenium is analyzed by fluorometric measurement.

12. The method of claim 11 wherein said measurement is performed on samples prepared by converting the selenium in the complexes to selenities, reacting the selenities with diaminonphthalene to obtain 4,5-benzopiazselenol for said fluorometric measurement.

* * * * *